US010906864B2

(12) United States Patent
Batthyány et al.

(10) Patent No.: US 10,906,864 B2
(45) Date of Patent: Feb. 2, 2021

(54) NITROALKENE NON STEROIDAL ANTI-INFLAMMATORY DRUGS (NA-NSAIDS) AND METHODS OF TREATING INFLAMMATION RELATED CONDITIONS

(71) Applicants: Institut Pasteur de Montevideo, Montevideo (UY); Universidad de la República, Montevideo (UY)

(72) Inventors: Carlos Batthyány, Montevideo (UY); Gloria Virginia López, Montevideo (UY); Carlos Escande, Montevideo (UY); Jorge Rodriguez Duarte, Ciudad de la Costa (UY); Williams Arturo Porcal Quinta, Montevideo (UY); Rosina Dapueto Capuccio, Montevideo (UY); Germán Adrian Galliussi López, Montevideo (UY); María Pia Garat Nuñez, Montevideo (UY); Paulina Invernizzi, Montevideo (UY); Mariana Ingold, Montevideo (UY); Lucia Colella, Montevideo (UY)

(73) Assignees: INSTITUT PASTEUR DE MONTEVIDEO, Montevideo (UY); UNIVERSIDAD DE LA REPUBLICA, Montevideo (UY); Carlos Batthány, Montevideo (UY)

( * ) Notice: Subject to any disclaimer, the term of this patent is extended or adjusted under 35 U.S.C. 154(b) by 0 days.

(21) Appl. No.: 16/534,488

(22) Filed: Aug. 7, 2019

(65) Prior Publication Data
US 2019/0359552 A1 Nov. 28, 2019

Related U.S. Application Data

(63) Continuation of application No. 15/855,300, filed on Dec. 27, 2017, now Pat. No. 10,428,008.

(51) Int. Cl.
| | | |
|---|---|---|
| *A61K 31/195* | (2006.01) | |
| *C07C 205/54* | (2006.01) | |
| *A61P 29/00* | (2006.01) | |
| *C07C 229/60* | (2006.01) | |
| *C07C 205/53* | (2006.01) | |
| *C07C 233/01* | (2006.01) | |

(52) U.S. Cl.
CPC ............ *C07C 205/54* (2013.01); *A61P 29/00* (2018.01); *C07C 205/53* (2013.01); *C07C 229/60* (2013.01); *C07C 233/01* (2013.01)

(58) Field of Classification Search
CPC ... C07C 205/53; C07C 205/54; C07C 233/01; C07C 229/60; A61P 29/00
USPC .................................. 514/564; 562/61, 434
See application file for complete search history.

(56) References Cited

U.S. PATENT DOCUMENTS

2019/0194121 A1 6/2019 Batthyány et al.

OTHER PUBLICATIONS

Sathish et al , The Journal of Organic Chemistry , Iron-Mediated One-Pot Synthesis of 3,5-Diarylpyridines from β-Nitrostyrenes, Feb. 2016, p. 2159-2165 (Year: 2016).*

(Continued)

*Primary Examiner* — Taylor V Oh
(74) *Attorney, Agent, or Firm* — Cozen O'Connor

(57) ABSTRACT

Nitroalkene non-steroidal anti-inflammatory compounds, pharmaceutical compositions thereof, and methods of treating inflammation related conditions.

4 Claims, 12 Drawing Sheets

(56) References Cited

OTHER PUBLICATIONS

Park et al., "tans-beta-Nitrostyrene Derivatives as Slow-Binding Inhibitors of Protein Tyrosine Phosphates," Biochemistry 43:15014-15021 (2004).
Celano, L., et al., "Analgesic and Anti-Inflammatory Properties of Arylnitoalkenes," Inflammatory Allergy Drug Targets 14(1):19-28 (2014).
Tsekhanskii, R.S., et al., "Mechanism of the action of alkaline solutions of sulfur on the nitro derivatives of toluene and diphenylmethane," Khimicheskayaw Tekhnoilogiya, 4:985-987 (1961).

* cited by examiner

NITROALKENE NON STEROIDAL ANTI-INFLAMMATORY DRUGS (NA-NSAIDS) AND METHODS OF TREATING INFLAMMATION RELATED CONDITIONS

CROSS REFERENCE TO RELATED APPLICATIONS

This application is a continuation of U.S. Non-Provisional application Ser. No. 15/855,300, filed Dec. 27, 2017. This application is related to co-pending U.S. Non-Provisional application Ser. No. 15/784,685 filed on Oct. 16, 2017 and International Application No. PCT/IB2017/056417 filed on Oct. 16, 2017, both of which claim priority to U.S. Provisional Application No. 62/408,459 filed on Oct. 14, 2016 and U.S. Provisional Application No. 62/570,973 filed on Oct. 11, 2017. U.S. Non-Provisional application Ser. No. 15/784,685, International Application No. PCT/IB2017/056417, U.S. Provisional Application No. 62/408,459, and U.S. Provisional Application No. 62/570,973 are all incorporated by reference in their entireties.

BACKGROUND

Common chronic inflammatory diseases ("CIDs") such as, inter alia, atherosclerosis, type 2 diabetes, asthma, gouty arthritis, kidney diseases, lupus, and inflammatory diseases of the central nervous system ("CNS"), pose a large risk and burden to afflicted patients because of its long-term debilitating illness that results in increased mortality and high health care costs. CIDs often involve a low-grade, controlled, and chronic systemic inflammatory state, which is generated by the activation of the pro-inflammatory transcription factor NF-κB and the inflammasome (a cytosolic supramolecular platform responsible of the production of interleukin (IL) 1β and 18 (IL-1β, IL-18)). However, as opposed to short term acute inflammation or infections, which illicit an immediate healing response to overcome a disease, the slow systemic progression of CIDs often preclude an adaptive healing response, which leads to chronic disease sequelae. Currently, classical NSAIDs that provide analgesic (pain-killing) and antipyretic (fever-reducing) effects, and, in higher doses, anti-inflammatory effects, are not recommended for the therapy of these diseases.

Thus, the scope of the present invention includes nitroalkene NSAID compounds and methods of treating inflammation related conditions, such as low grade chronic inflammation that underlies most non-transmissible CIDs.

SUMMARY

One embodiment within the scope of the invention is a compound of Formula I:

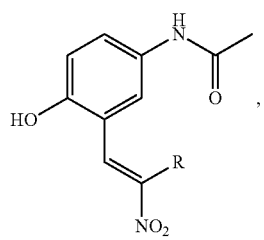

I wherein R is hydrogen or a $C_{1-11}$ alkyl, or a pharmaceutically acceptable salt thereof.

In another embodiment the invention is a compound of Formula II:

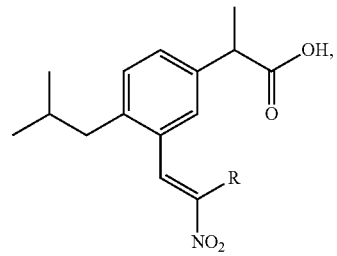

II wherein R is hydrogen or a $C_{1-11}$ alkyl, or a pharmaceutically acceptable salt.

One embodiment within the scope of the invention is a compound of Formula III:

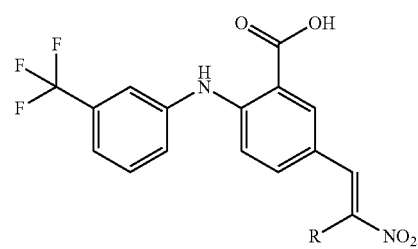

III where R is hydrogen or a $C_{1-11}$ alkyl, or a pharmaceutically acceptable salt thereof.

In another embodiment within the scope of the invention is a compound of Formula IV:

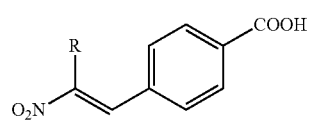

IV where R is hydrogen or a $C_{1-11}$ alkyl, or a pharmaceutically acceptable salt thereof.

In another embodiment within the scope of the invention is a compound of Formula V:

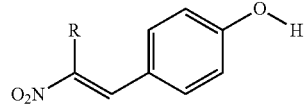

V where R is hydrogen or a $C_{1-11}$ alkyl, or a pharmaceutically acceptable salt thereof.

One embodiment within the scope of the present invention is a method of treating inflammation related conditions comprising administering to a subject in need thereof a therapeutically effective amount of a nitroalkene nonsteroidal anti-inflammatory drug.

DESCRIPTION

Figure 1:
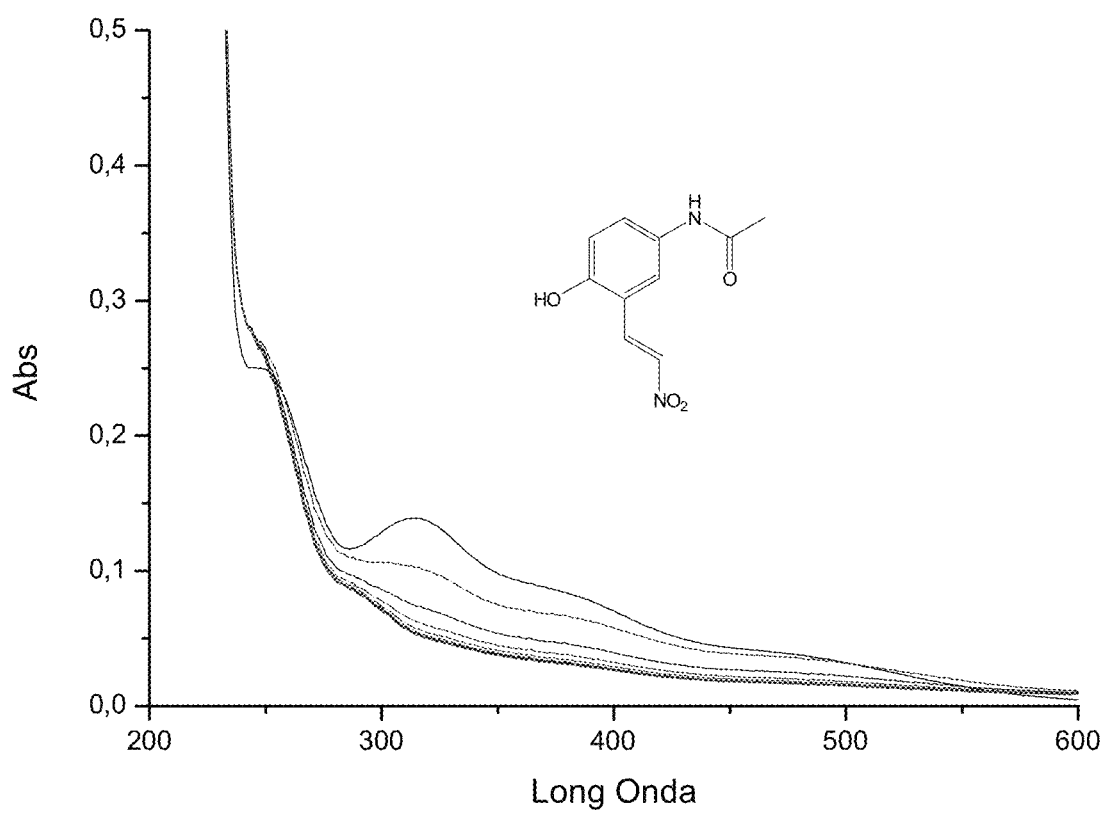
FIG. 1 depicts the spectrograph of a reaction of PARANA (30 μM) with beta-mercaptoethanol (30 μM) in Phosphate Buffer 100 mM pH 7.4 followed spectrophotometrically (each spectra every 60 sec).
Figure 2:
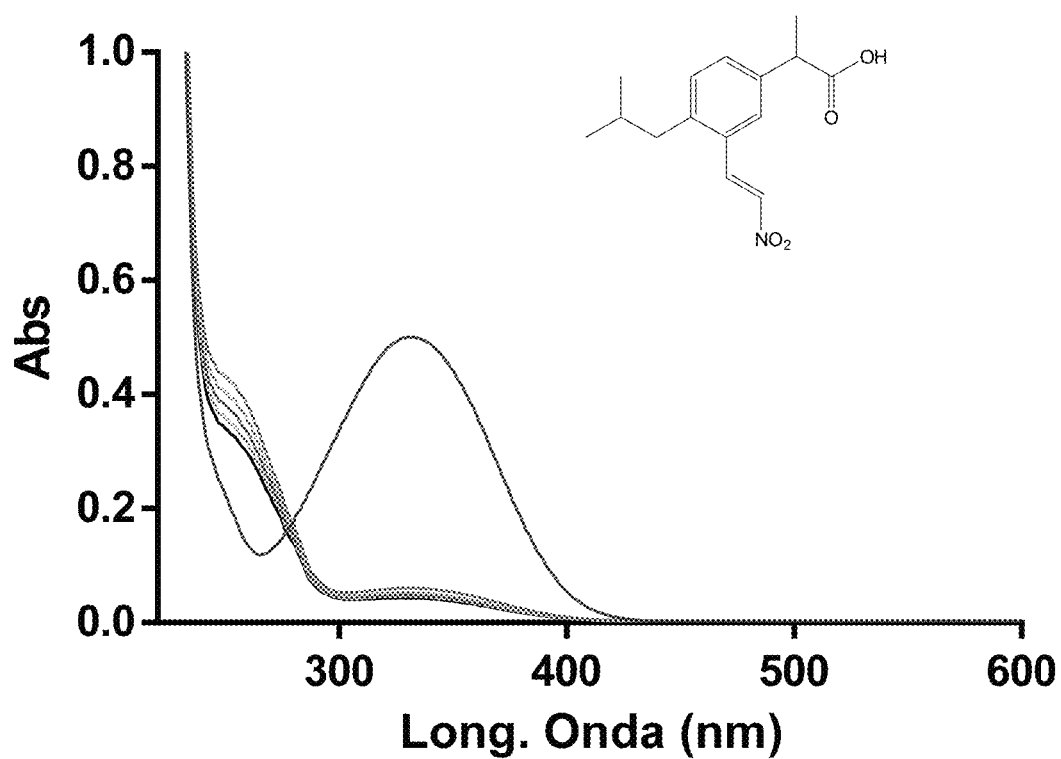
FIG. 2 depicts the spectrograph of a reaction of IBUNA (50 μM) with beta-mercaptoethanol (250 μM) in Phosphate Buffer 100 mM pH 7.4 followed spectrophotometrically (each spectra every 60 sec).
Figure 3:
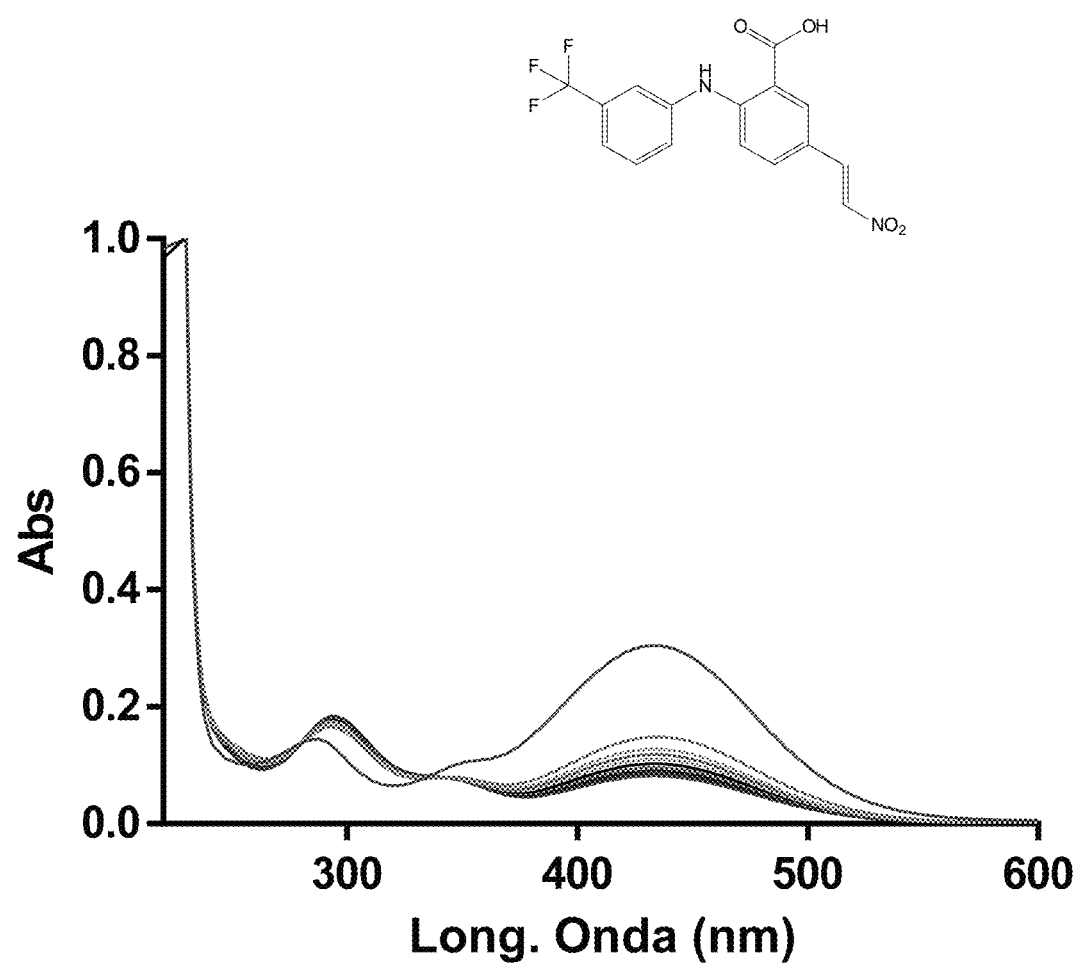
FIG. 3 depicts the spectrograph of a reaction of FluFENA (12.5 μM) with beta-mercaptoethanol (125 μM) in Phosphate Buffer 100 mM pH 7.4 followed spectrophotometrically (each spectra every 60 sec).
Figure 4:
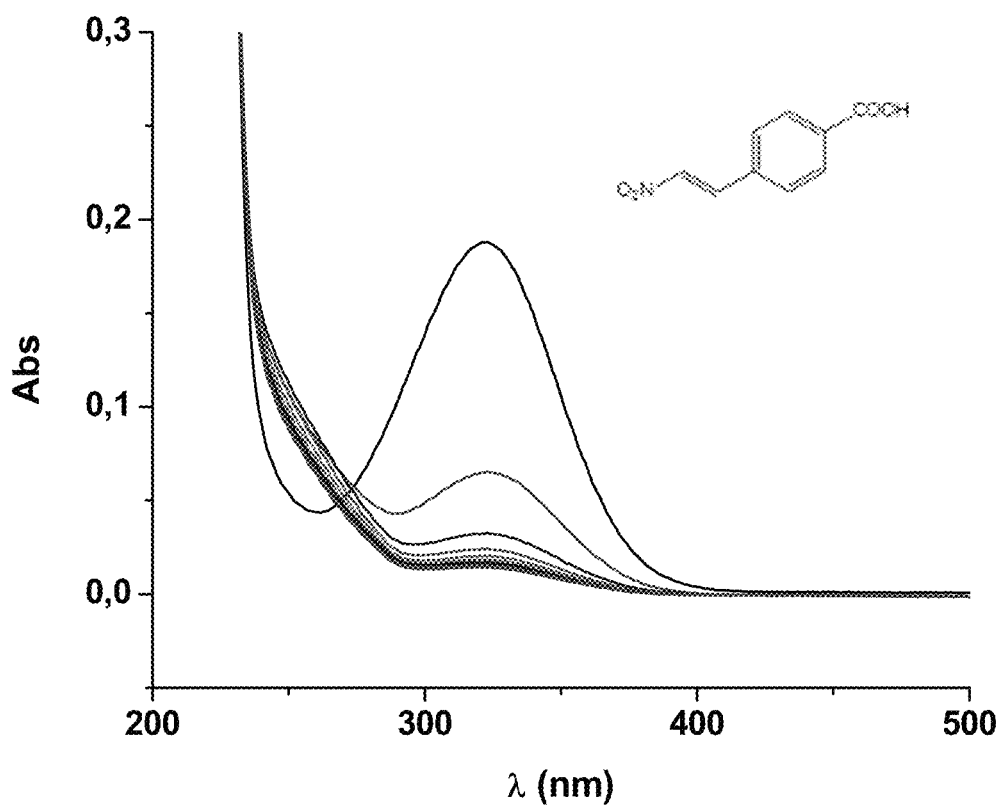
FIG. 4 depicts the spectrograph of a reaction of BANA (10 μM) with beta-mercaptoethanol (30 μM) in Phosphate Buffer 100 mM pH 7.4 followed spectrophotometrically (each spectra every 60 sec).
Figure 5:
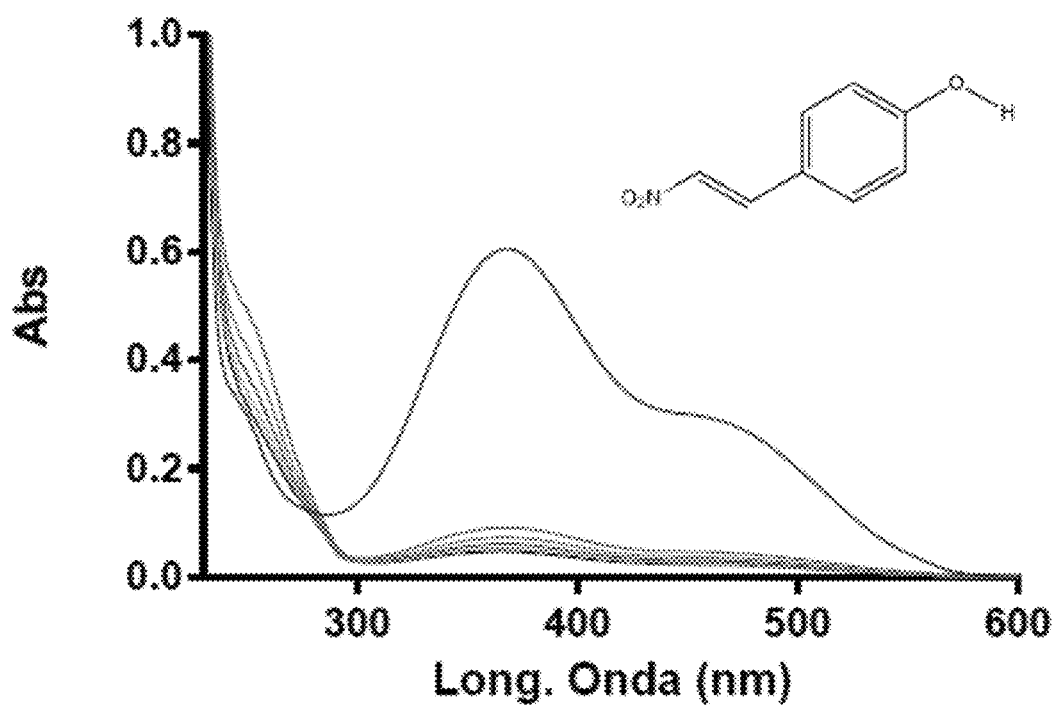
FIG. 5 depicts the spectrograph of a reaction of PheNA (50 μM) with beta-mercaptoethanol (500 μM) in Phosphate Buffer 100 mM pH 7.4 followed spectrophotometrically (each spectra every 60 sec).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications that may be mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

The term "subject," as used herein, describes an organism, including mammals, to which treatment with the compositions and compounds according to the subject disclosure can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The optical isomers with the scope of the present invention can be obtained by resolution of the racemic mixtures according to conventional processes, for example by formation of diastereoisomeric salts by treatment with an optically active base and then separation of the mixture of diastereoisomers by crystallization, followed by liberation of the optically active bases from these salts. Another method calls for chiral separation of the enantiomers with the use of a chiral chromatography column optimized to maximize the separation of the enantiomers. Optimization of the chromatographic method of chiral resolution is routine for one of ordinary skill in the art. Yet another method for isolating optical isomers is by distillation, crystallization or sublimation if a physical property of the enantiomers is different. The optically active compounds within the scope of the present invention can also be obtained by utilizing optically active starting materials. The isomers may be in the form of a free acid, a free base, an ester or a salt.

Also included in the compounds within the scope of the present invention and the stereoisomers are the pharmaceutically-acceptable salts thereof. The term "pharmaceutically-acceptable salts" embraces salts commonly used to form alkali metal salts and to form additional salts of free acids or free bases. The nature of the salt is not critical, provided that it is pharmaceutically-acceptable. Suitable pharmaceutically-acceptable acid addition salts of compounds within the scope of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may include aliphatic, cycloaliphatic, aromatic, araliphatic, heterocyclic, carboxylic and sulfonic classes of organic acids. Examples of such organic acids include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydrobenzoic, phylacetic, mandelic, embonic, methanesulfonic, ethanesulfonic, benzenesulfonic, pantothenic, 2-hydroxyethanesulfonic, toluenesulfonic, sulfanilic, cyclohyexylaminosuflonic, stearic, algenic, (3-hydrobutyric, galactaric and galacturnoic acid. Suitable pharmaceutically-acceptable base addition salts of compounds within the scope of the present invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, triethylamine, trimethylamine. All the listed salts of the corresponding compound of the invention may be prepared by conventional means known to one of ordinary skill in the art. One example of a conventional method of salt formation is by reacting the appropriate acid or base with a compounds within the scope of the present invention at various mole ratios. Another method is by using different mole ratios of the appropriate acid or base in various solvent systems to control the concentration of the dissociated species of a compound within the scope of the present invention to maximize salt formation. The present invention also contemplates crystalline forms of the salts described herein.

Crystalline forms of compounds within the scope of the present invention, may also include but are not limited to hydrates, solvates, and co-crystals. Crystalline solvates include solvents including but not limited to the following: MeOH, EtOH, AcOH, EtOEt, AcOEt, acetone, DMSO, DMF, MeCN, $CH_2Cl_2$, $CHCl_3$, $CCl_4$, dioxane, THF, benzene, toluene, p-xylene, and hexane.

Crystalline hydrates and solvates may be stoichiometric as according to the mole ratio of the water or organic solvent molecule to the compound or salt thereof. The crystalline hydrate may also be non-stoichiometric depending on the conditions of the unit cell which result in a thermodynamically or kinetically stable crystal. Crystalline salts and co-crystals may also be stoichiometric or non-stoichiometric for reasons stated above. One of skill in the art of crystallography understands that the components in the unit cell of a crystal may or may not be stoichiometric depending on the conditions that stabilize a crystal.

Administration and Compositions

The compounds and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g.

powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in Remington: *The Science and Practice of Pharmacy*, 21$^{st}$ edition (Lippincott Williams & Wilkins, 2006).

Therapeutic compounds can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may treat inflammation related conditions such as, but not limited to, CIDs.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an the active agent of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

Further embodiments which may be useful for oral administration of the active agent include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids may have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko).

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to a monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include the active agent administered in combination with other active such as, for example, adjuvants, protease inhibitors, NSAIDs, steroid anti-inflammatory drugs (SAIDs), or other compatible drugs or compounds where such combination is seen to be desirable or advantageous in achieving the desired effects of the methods described herein.

Other embodiments of the present invention include a pharmaceutical composition comprising an effective amount of the active agent and one or more pharmaceutically acceptable excipient. Other embodiments include a pharmaceutical composition comprising an effective amount of pharmaceutically-acceptable salts of the active agent. Other embodiments include a pharmaceutical composition comprising an effective amount of pharmaceutically-acceptable salts of active agent and a pharmaceutically-acceptable excipient.

In yet other embodiments, the active agent may be combined with one or more secondary therapeutic agents. Secondary therapeutic agents my include but are not limited to: an anti-platelet agent, an inhibitor of angiotensin II, an ACE inhibitor, a $Ca^{++}$ channel blocker, an insulin sensitizer, a HMG-CoA reductase inhibitor, a beta blocker, a non-steroidal anti-inflammatory drug, a steroidal anti-inflammatory drug, peroxisome proliferator-activated receptors (PPAR) modulators, and combinations thereof.

Nitroalkene NSAID compositions as described herein may be administered to subjects to treat a number of both acute and chronic inflammatory and metabolic conditions. In some embodiments, the compounds within the scope of the described invention and pharmaceutical compositions thereof as described herein may be used to treat inflammation related conditions, including but not limited to, auto-immune disease, auto-inflammatory disease, arterial stenosis, organ transplant rejection and burns, and chronic conditions such as, chronic lung injury and respiratory distress, diabetes, hypertension, obesity, arthritis, atherosclerosis, asthma, gouty arthritis, kidney diseases, lupus, inflammatory diseases of the system central nervous system (CNS), neurodegenerative disorders, and various skin disorders.

However, in other embodiments, the nitroalkene NSAID compounds and pharmaceutical compositions thereof as described herein may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, post-surgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

The compounds within the scope of the described invention and pharmaceutical compositions thereof as described herein may be administered to subjects to treat inflammation related conditions such as, but not limited to, CIDs.

General Synthetic Procedures

In general, the synthetic route by which the nitroalkene NSAIDs are obtained starts with the formylation of an NSAID aromatic ring followed by a condensation reaction of the prepared aldehyde with a nitroalkane.

One such synthetic route follows the following steps:

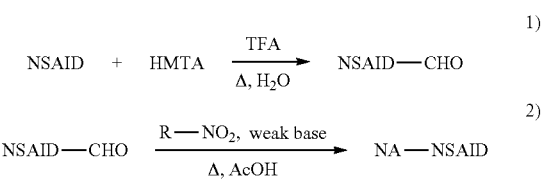

The scheme depicted above demonstrates a process of formylating aromatic compounds with hexamethylenetetramine ("HMTA") and trifluoroacetic acid ("TFA") followed by a base-catalyzed condensation reaction of the aldehyde ("NSAID-CHO") with a nitroalkane ("R—NO$_2$") in glacial acetic acid ("AcOH") to produce the desired nitroalkene NSAID ("NA-NSAID"). Although various weak bases and nitroalkanes of various carbon lengths can be used, the preferred nitroalkane and weak base are nitromethane and ammonium acetate, respectively, as shown infra. When the corresponding aldehyde is commercially available, it is not necessary to perform step 1. Another procedure for the synthesis of nitroalkene NSAID is illustrated in Example 2 below. It is well within the knowledge and skill of a person of ordinary skill in the art to prepare the aldehyde and perform the subsequent condensation reaction to synthesize nitroalkene NSAIDs.

EXAMPLES

The following examples contain detailed methods of preparing compounds within the scope of the present invention. These detailed descriptions serve to exemplify the above general synthetic schemes which form part of the invention. These detailed descriptions are presented for illustrative purposes only and are not intended as a restriction on the scope of the invention. All parts are by weight and temperatures are in Degrees Celsius unless otherwise indicated. All compounds showed NMR spectra consistent with their assigned structures.

Example 1

(E)-N-(4-hydroxy-3-(2-nitrovinyl)phenyl)acetamide (PARANA)

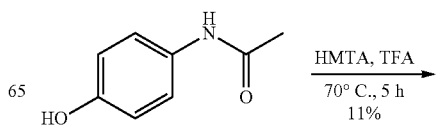

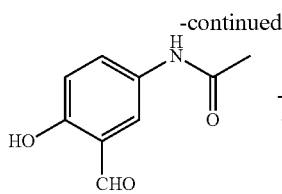

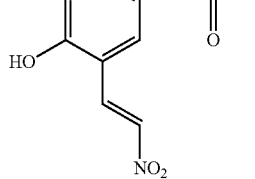

N-(3-formyl-4-hydroxyphenyl)acetamide. To a solution of N-(4-hydroxyphenyl)acetamide (6.6 mmol) in TFA (4 mL), in an ice-bath, HMTA (26 mmol) was added portionwise. The reaction mixture is heated to 70° C. for 5 h, allowed to cool to room temperature (rt) and poured into water (20 mL). Then, it was extracted with ethyl acetate (3×20 mL). The combined organic extracts were washed with brine and dried over sodium sulfate. The crude product was purified by silica flash column chromatography (hexane:ethyl acetate, 1:1) to render the desire product (133 mg, 11%). $^1$H NMR (400 MHz, acetone-d6) δ 10.73 (s, 1H), 10.01 (s, 1H), 9.24 (s, 1H), 8.16 (d, J=2.7 Hz, 1H), 7.70 (dd, J=8.9, 2.7 Hz, 1H), 6.94 (d, J=8.9 Hz, 1H), 2.09 (s, 3H).

(E)-N-(4-hydroxy-3-(2-nitrovinyl)phenyl)acetamide. To a solution of N-(3-formyl-4-hydroxyphenyl)acetamide (0.18 mmol) in nitromethane (0.1 mL) is added glacial acetic acid (0.1 mL) and ammonium acetate (0.11 mmol). The solution is heated at 110° C. for 1 hour. Ice-water is added to the reaction mixture, and then extracted with ethyl acetate, dried over sodium sulfate and concentrated under reduced pressure to give the desire product with high purity (32 mg, 80%). $^1$H NMR (400 MHz, acetone-d6) δ 9.66 (s, 1H); 9.14 (s, 1H); 8.16 (d, J=13.5 Hz, 1H); 8.01 (d, J=13.5 Hz, 1H); 7.88 (d, J=2.3 Hz, 1H); 7.62 (dd, J=2.3, 8.8 Hz, 1H); 7.00 (d, J=8.8 Hz, 1H); 2.06 (s, 3H). $^{13}$C NMR (100 MHz, acetone-d6) δ 167.84, 153.93, 138.03, 135.20, 132.55, 125.17, 122.22, 117.03, 116.37, 23.11.

Example 2

(E)-2-(4-isobutyl-3-(2-nitrovinyl)phenyl)propanoic acid (IBUNA)

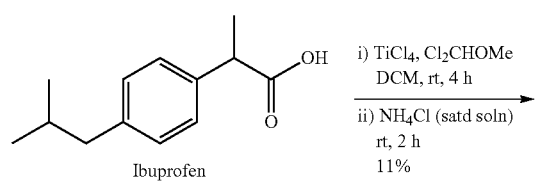

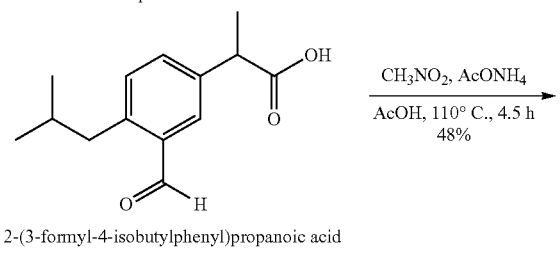

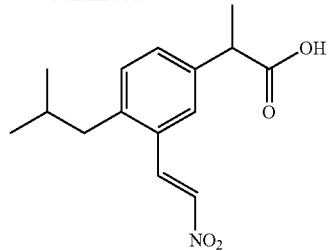

(E)-2-(4-isobutyl-3-(2-nitrovinyl)phenyl)propanoic acid 2-(3-formyl-4-isobutylphenyl)propanoic acid. Ibuprofen (4.8 mmol) was dissolved in dry DCM (13 mL), purged with $N_2$, and cooled with an ice bath to 0° C. A solution of TiCl$_4$ 1.0 M in DCM (21.5 mL) was added dropwise. The reaction mixture was stirred for 1 h. Then, dichloromethyl methyl ether (1 mL) was added, and the mixture was left to react for 4 h. Next, 40 mL of a saturated solution of NH$_4$Cl was added and left stirring for 2 h. The organic layer was separated and washed with 0.1 N HCl solution (15 mL) and brine (15 mL). The organic layer was dried over sodium sulfate and filtered, and the solvent was evaporated under reduced pressure. The crude product was purified by silica flash column chromatography (ethyl acetate:hexane gradient) to give the desired product (123 mg, 11%). $^1$H NMR (400 MHz, CDCl$_3$) δ 10.30 (s, 1H), 7.82 (d, J=2.1 Hz, 1H), 7.49 (dd, J=7.9, 2.1 Hz, 1H), 7.23 (d, J=7.9 Hz, 1H), 3.82 (q, J=7.2 Hz, 1H), 2.89 (d, J=7.2 Hz, 2H), 1.90-1.80 (m, 1H), 1.56 (d, J=7.2 Hz, 3H), 0.96 (s, 3H), 0.94 (s, 3H). $^{13}$C NMR (100 MHz, CDCl$_3$) δ 191.97, 179.21, 143.80, 138.18, 134.12, 132.73, 132.31, 129.88, 44.66, 40.86, 31.17, 22.36, 18.03.

(E)-2-(4-isobutyl-3-(2-nitrovinyl)phenyl)propanoic acid. To a solution of 2-(3-formyl-4-isobutylphenyl)propanoic acid (0.7 mmol) in nitromethane (1 mL) is added glacial acetic acid (3 mL) and ammonium acetate (2.1 mmol). The solution is heated at 110° C. for 4.5 hours. Ice-water is added to the reaction mixture, and then extracted with ethyl acetate, dried over sodium sulfate and concentrated under reduced pressure. The crude product was purified by silica flash column chromatography (ethyl acetate:hexane gradient) to give the desire product (97 mg, 48%). $^1$H NMR (400 MHz, CDCl$_3$) δ 8.32 (d, J=13.5 Hz, 1H), 7.54 (d, J=13.5 Hz, 1H), 7.48 (d, J=1.8 Hz, 1H), 7.39 (dd, J=7.8, 1.8 Hz, 1H), 7.23 (d, J=7.8 Hz, 1H), 3.77 (q, J=7.2 Hz, 1H), 2.64 (d, J=7.2 Hz, 2H), 1.86-1.76 (m, 1H), 1.56 (d, J=7.2 Hz, 3H), 0.96 (s, 3H), 0.94 (s, 3H). $^{13}$C NMR (100 MHz, CDCl$_3$) δ 179.65, 142.31, 138.32, 137.84, 136.59, 131.93, 130.85, 129.00, 126.33, 44.75, 42.18, 30.78, 22.36, 18.08. MS (EI, 70 eV): m/z (%) 277 (M+, 6).

Example 3

(E)-5-(2-nitrovinyl)-2-((3-(trifluoromethyl)phenyl)amino)benzoic acid (FluFENA)

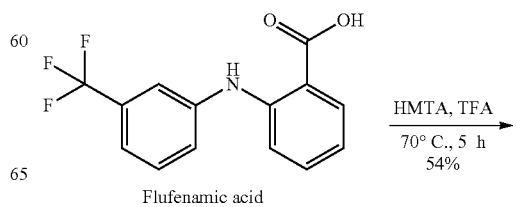

Flufenamic acid

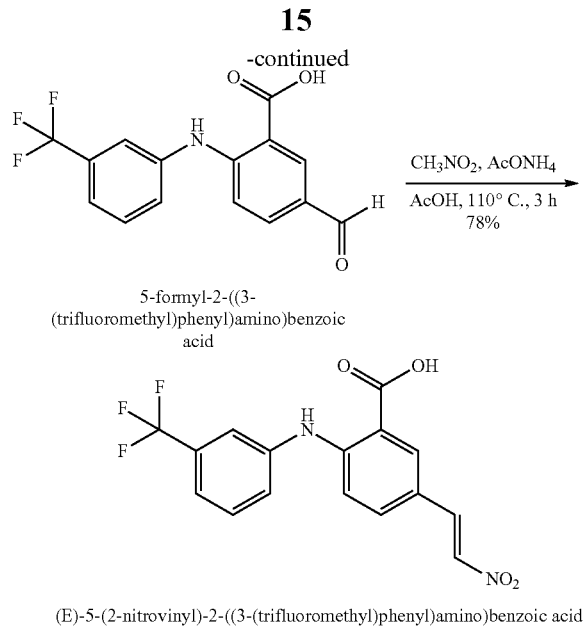

5-formyl-2-((3-(trifluoromethyl)phenyl)amino)benzoic acid (E)-5-(2-nitrovinyl)-2-((3-(trifluoromethyl)phenyl)amino)benzoic acid 5-formyl-2-((3-(trifluoromethyl)phenyl)amino)benzoic acid. To a solution of flufenamic acid (18 mmol) in TFA (0.5 mL), in an ice-bath, HMTA (7 mmol) was added portionwise. The reaction mixture is heated to 70° C. for 5 h, allowed to cool to rt and poured into water (15 mL). Then, it was extracted with ethyl acetate (3×15 mL). The combined organic extracts were washed with brine and dried over sodium sulfate. The crude product was purified by silica flash column chromatography (hexane:ethyl acetate, 8:2) to render the desire product (298 mg, 54%). $^1$H NMR (400 MHz, acetone-d6) δ 10.41 (s, 1H), 9.88 (s, 1H), 8.59 (d, J=1.8 Hz, 1H), 7.95 (dd, J=8.8, 1.8 Hz, 1H), 7.70 (m, 3H), 7.57 (m, 1H), 7.37 (dd, J=8.8 Hz, 1H). $^{13}$C NMR (100 MHz, acetone-d6) δ 189.36, 169.08, 151.90, 140.26, 135.86, 134.12, 130.69, 127.29, 127.01, 121.41, 121.37, 119.99, 119.95, 113.61.

(E)-5-(2-nitrovinyl)-2-((3-(trifluoromethyl)phenyl)amino)benzoic acid. To a solution of 5-formyl-2-((3-(trifluoromethyl)phenyl)amino)benzoic acid (1 mmol) in nitromethane (1 mL) is added glacial acetic acid (4 mL) and ammonium acetate (2.9 mmol). The solution is heated at 110° C. for 3.5 hours and allowed to cool to rt. An orange precipitate appear on cooling, was filtered-off and washed with water and dried to give the desired product with high purity (264 mg, 78%). $^1$H NMR (400 MHz, DMSO-d6) δ 13.57 (s, 1H), 10.22 (s, 1H), 8.36 (d, J=1.9 Hz, 1H), 8.13 (d, J=13.5 Hz, 1H), 8.09 (d, J=13.5 Hz, 1H), 7.94 (dd, J=8.9, 1.9 Hz, 1H), 7.64 (m, 3H), 7.50 (m, 1H), 7.23 (d, J=8.9 Hz, 1H). $^{13}$C NMR (100 MHz, DMSO-d6) δ 169.62, 149.54, 140.71, 139.55, 136.23, 135.72, 134.86, 131.19, 131.00, 130.69, 126.62, 125.75, 123.04, 121.09, 120.43, 119.37, 114.83, 114.00. MS (EI, 70 eV): m/z (%) 352 (M+, 100).

Example 4

(E)-4-(2-nitrovinyl)benzoic acid (BANA)

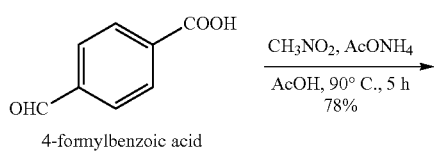

4-formylbenzoic acid

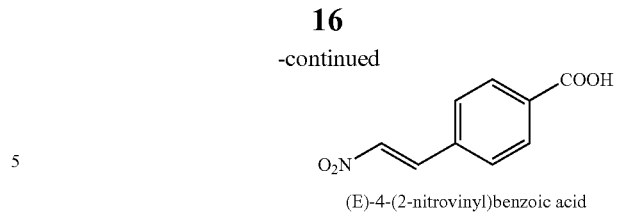

(E)-4-(2-nitrovinyl)benzoic acid

To a stirred solution of ammonium acetate (32 mmol), nitromethane (20 mL) and glacial acetic acid (39 mL) at 90° C., 4-formylbenzoic acid (26 mmol) was added portionwise and maintain at 90° C. for 5 hours. Then, the reaction mixture was allowed to cool to rt. A yellow precipitate appear on cooling, was filtered-off and washed with water and dried to give the desired product with high purity (3.93 g, 78%). $^1$H NMR (400 MHz, CDCl$_3$) δ 8.30 (d, J=13.7 Hz, 1H), 8.18 (d, J=13.7 Hz, 1H), 8.00 (d, J=8.6 Hz, 2H), 7.97 (d, J=8.6 Hz, 2H). $^{13}$C NMR (100 MHz, CDCl$_3$) δ 167.07, 140.12, 138.30, 134.88, 133.80, 130.30 (2C), 130.26 (2C).

Example 5

(E)-4-(2-nitrovinyl)phenol (PheNA)

An analogous procedure as shown in Example 4 is performed with 4-hydroxybenzaldehyde to produce (E)-4-(2-nitrovinyl)phenol as a yellow solid (yield 68%). $^1$H NMR (400 MHz, CDCl$_3$) δ 9.26 (s, 1H), 8.04 (d, J=13.5 Hz, 1H), 7.84 (d, J=13.5 Hz, 1H), 7.72 (d, J=8.6 Hz, 1H), 6.97 (d, J=8.6 Hz, 1H).

Biologic Activity

The following methods described are used in order to demonstrate biological activity and therapeutic use, and should not to be construed in any way as limiting the scope of the invention. While not wishing not to be bound by theory, the generation of the low grade, sterile, chronic inflammatory state underlying CIDs is the activation of the pro-inflammatory transcription factor NF-κB and the inflammasome (a cytosolic supramolecular platform responsible of the production of interleukin (IL) 1β and 18 (IL1β, IL18)). The following studies demonstrate the role of nitroalkene NSAIDs in reducing the pro-inflammatory activity regulated by NF-κB and the inflammasome.

In Vitro Activity

While not wishing to be bound by theory, during inflammation, reversible reactions with nucleophilic molecules such as NF-κB and the inflammasomes have shown to modify inflammatory response. One method to identify reactions with nucleophilic targets at physiological pH is by screening with beta mercaptoethanol ("BME"). As shown in FIGS. 1-4, nitroalkene NSAIDs form adducts with beta mercaptoethanol ("BME"), The reactions demonstrating nitroalkene NSAID adduction to BME depicted by FIGS. 1-5 included reacting 30 μM of PARANA with 30 μM of BME in 100 mM phosphate buffer at pH 7.4, 50 μM of IBUNA with 250 μM of BME in 100 mM phosphate buffer at pH 7.4, 12.5 μM FluFENA with 125 μM BME in 100 mM phosphate buffer at pH 7.4, 10 μM of BANA with 30 μM of BME in 100 mM of phosphate buffer at pH 7.4, and 50 μM of PheNA with 500 μM of BME in 100 mM phosphate buffer at pH 7.4. All reactions showed an absorbance increase which denoted nitroalkene NSAID adduction with BME. Thus, the nitroalkene NSAIDs within the scope of the present invention react with nucleophilic molecules such as NF-κB and the inflammasomes to modify inflammatory response.

Figure 6:
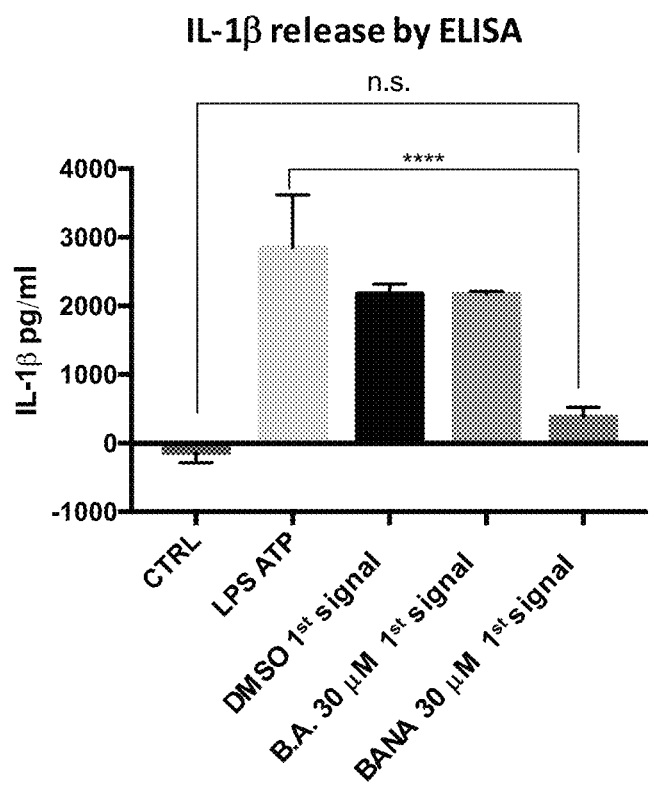
FIG. 6 illustrates inflammasome modulation by BANA after stimulation by LPS (1st signal).
Figure 7:
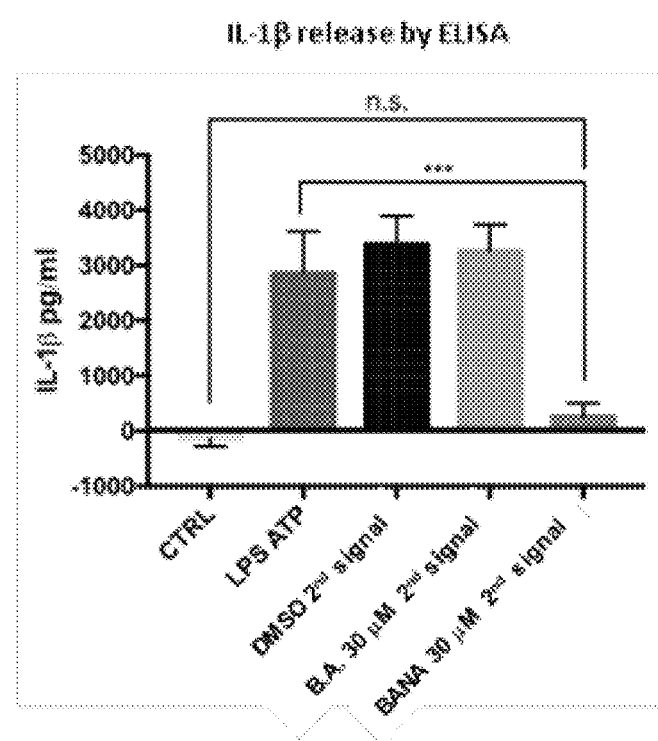
FIG. 7 illustrates inflammasome modulation by BANA after stimulation by ATP (2nd signal).

Further in vitro studies demonstrated the unexpected advantage of the nitroalkene NSAIDs over non-nitroalkenylated NSAIDs to downregulate secretion of pro-inflammatory cytokines. In order to compare benzoic acid (BA) and nitroalkene benzoic acid (BANA) over NF-κB and inflammasome function in macrophages, THP-1 cells were differentiated into macrophages with PMA (200 nM, 48 h). Cells were then stimulated with LPS (250 ng/mL) and with ATP (5 mM, 45 minutes). Together with LPS (1st signal, FIG. 6) or ATP (2nd signal, FIG. 7), cells were treated with Benzoic acid (30 μM) or BANA (30 μM). Supernatants were collected and IL-1β secretion was measured by ELISA. According to the results, the inhibition of IL-1β secretion in cells stimulated by LPS demonstrated the ability of BANA to prevent NF-κB nuclear translocation, which is a crucial step in the generation of the inflammasome. The inhibition of IL-1β secretion in cells stimulated by ATP demonstrated the direct inhibition of the inflammasome. Thus, BANA inhibits both the generation of the inflammasome, and inhibits the inflammasome itself.

Figure 8:
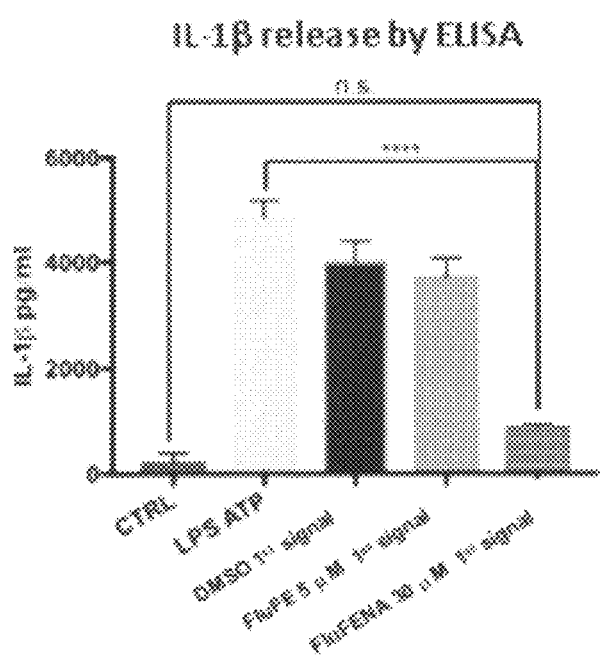
FIG. 8 illustrates inflammasome modulation by FluFENA after stimulation by LPS (1st signal).
Figure 9:
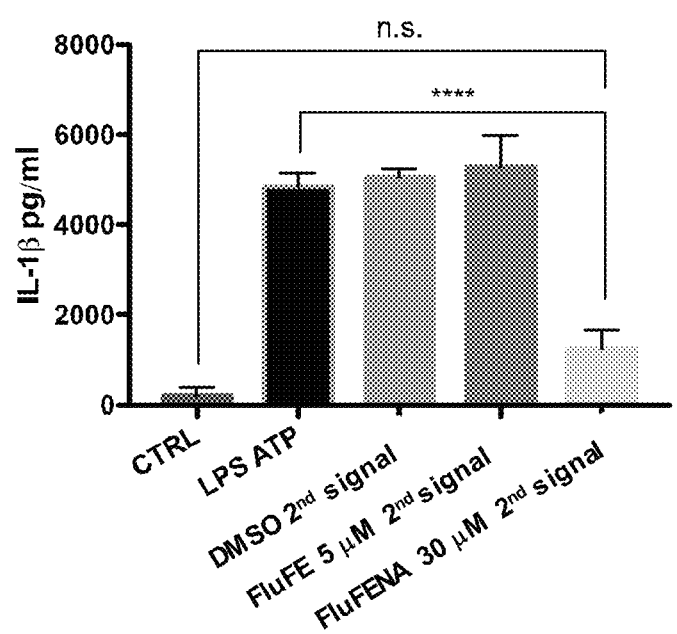
FIG. 9 illustrates inflammasome modulation by FluFENA after stimulation by ATP (2nd signal).

Further exemplary studies were performed with Flufenamate (FluFE) and nitroalkene flufenamate (FluFENA). In order to study the effect of Flufenamate (FluFE) and FluFENA over NF-κB and inflammasome function in macrophages, THP-1 cells were differentiated into macrophages with PMA (200 nM, 48 h). Cells were stimulated with LPS (250 ng/mL) and then with ATP (5 mM, 45 minutes). Together with LPS (1st signal, FIG. 8) or ATP (2nd signal, FIG. 9), cells were treated with FluFE (5 μM) or FluFENA (5 Supernatant were collected and IL-1β secretion was measured by ELISA. Cell viability was assessed by the MTT assay. Again, the resulting data demonstrates the unexpected advantage provided by the nitroalkene NSAID.

Figure 10:
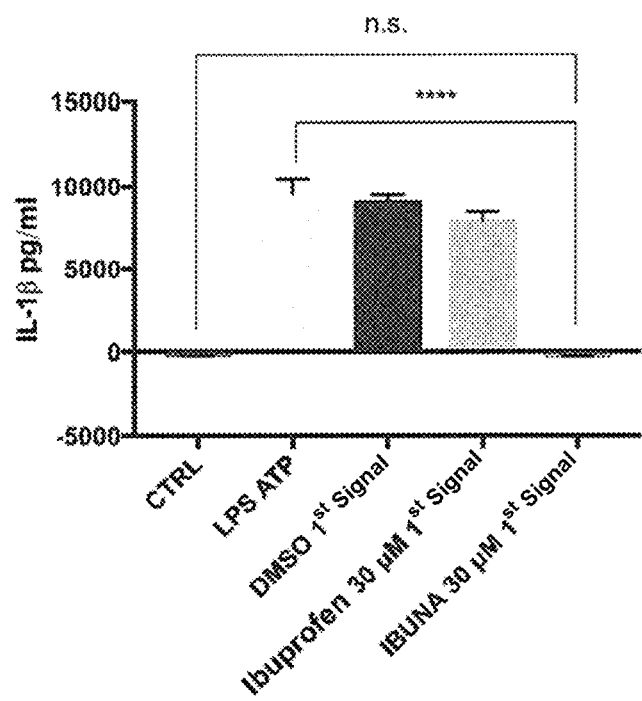
FIG. 10 illustrates inflammasome modulation by IBUNA after stimulation by LPS (1st signal).
Figure 11:
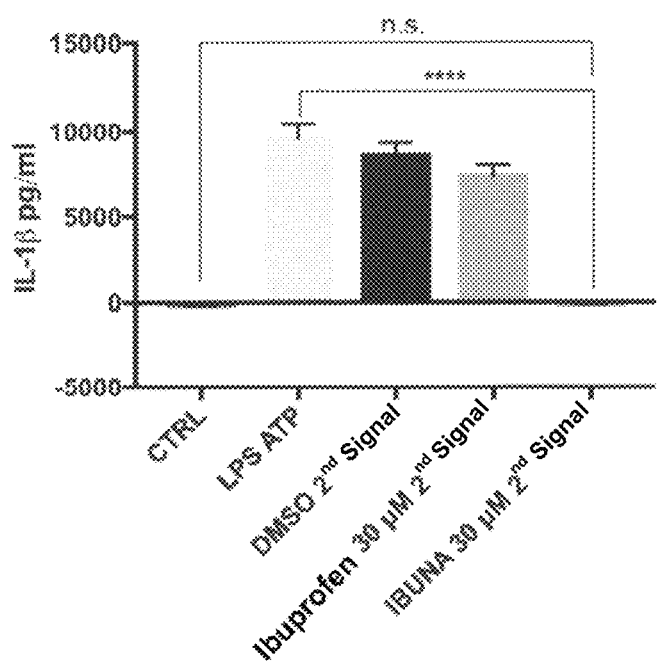
FIG. 11 illustrates inflammasome modulation by IBUNA after stimulation by ATP (2nd signal).

FIG. 10 and FIG. 11 further demonstrate the unexpected superiority of nitroalkene NSAIDs of non-alkenylated NSAIDs. To study the effect of ibuprofen and IBUNA over NF-κB and inflammasome function in macrophages, THP-1 cells were differentiated into macrophages with PMA (200 nM, 48 h). Cells were stimulated with LPS (250 ng/mL) and then with ATP (5 mM, 45 minutes). Together with LPS (1st signal, FIG. 10) or ATP (2nd signal, FIG. 11), cells were treated with Ibuprofen (20 μM) or IBUNA (20 Supernatant were collected and IL-1β secretion was measured by ELISA.

In Vivo Activity

Figure 12:
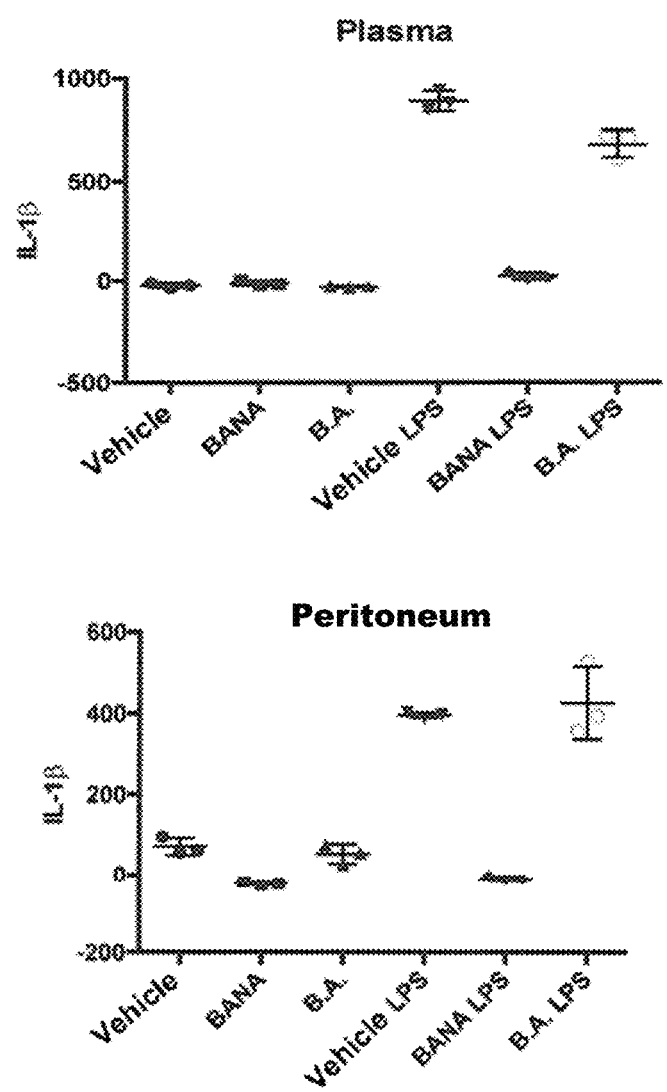
FIG. 12 demonstrates in vivo inhibition of IL-1β release in LPS-induced inflammatory response by BANA.

Unexpected superior anti-inflammatory effects of nitroalkene NSAIDs were further demonstrated by in vivo models. For example, FIG. 12 demonstrates the anti-inflammatory effects of BA or BANA in an in vivo model of peritonitis. Mice were treated with BANA, Benzoic Acid (50 mg/kg, IP) or the vehicle (100 mM Phosphate buffer 10% DMSO) for 1 hour. Then were injected with LPS (10 mg/kg, IP) or PBS for 2 hours. Mice were collected for peritoneal wash and blood samples were extracted. The peritoneal wash and plasma were stored to measure IL-1β by ELISA. The values are show as mean±SD from three mice per condition and we have used the statistic test one-way ANOVA with Bonferroni. FIG. 11 illustrates a marked decrease in the level of pro-inflammatory cytokine IL-1β secretion in mice treated with BANA as opposed to BA in both the blood plasma and the peritoneal wash.

The invention claimed is:

1. A method of treating chronic inflammation comprising administering to a subject in need thereof a therapeutically effective amount of a nitroalkene nonsteroidal anti-inflammatory drug (NA-NSAID) selected from the group consisting of:

a compound of Formula I:

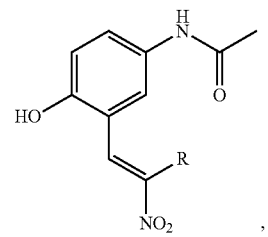

wherein R is hydrogen or a $C_{1-11}$ alkyl, or a pharmaceutically acceptable salt thereof;

a compound of Formula II:

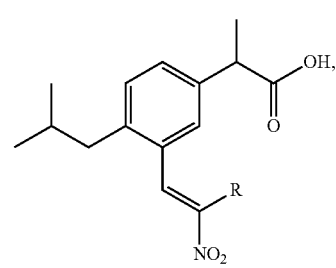

wherein R is hydrogen or a $C_{1-11}$ alkyl, or a pharmaceutically acceptable salt thereof;

a compound of Formula III:

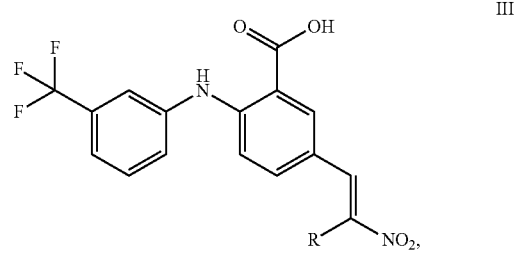

wherein R is hydrogen or a $C_{1-11}$ alkyl, or a pharmaceutically acceptable salt thereof;

a compound of Formula V:

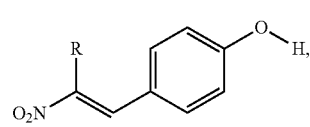

wherein R is hydrogen, or a pharmaceutically acceptable salt thereof; and any combination thereof.

2. The method of claim 1, wherein the nitroalkene nonsteroidal anti-inflammatory drug (NA-NSAID) is selected from the group consisting of:

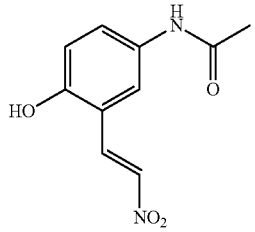 [SMILES: CC(=O)Nc1ccc(O)c(/C=C/[N+](=O)[O-])c1]

or a pharmaceutically acceptable salt thereof;

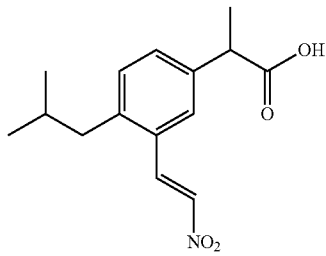 [SMILES: CC(C)Cc1ccc(C(C)C(=O)O)cc1/C=C/[N+](=O)[O-]]

or a pharmaceutically acceptable salt thereof;

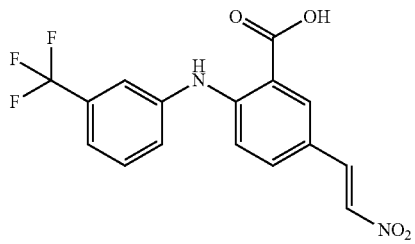 [SMILES: O=C(O)c1cc(/C=C/[N+](=O)[O-])ccc1Nc1cccc(C(F)(F)F)c1]

or a pharmaceutically acceptable salt thereof;

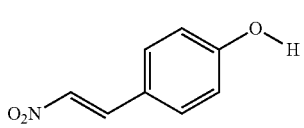 [SMILES: O=[N+]([O-])/C=C/c1ccc(O)cc1]

or a pharmaceutically acceptable salt thereof; and any combination thereof.

3. A method of treating chronic inflammation comprising administering to a subject in need thereof a pharmaceutical composition comprising a therapeutically effective amount of a nitroalkene nonsteroidal anti-inflammatory drug (NA-NSAID) selected from the group consisting of:

a compound of Formula I:

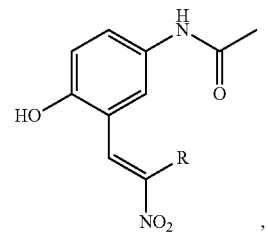

wherein R is hydrogen or a $C_{1-11}$ alkyl, or a pharmaceutically acceptable salt thereof;

a compound of Formula II:

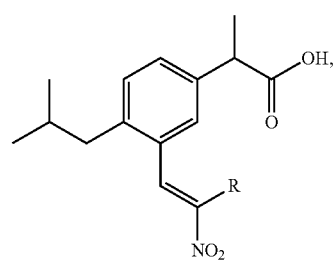

wherein R is hydrogen or a $C_{1-11}$ alkyl, or a pharmaceutically acceptable salt thereof;

a compound of Formula III:

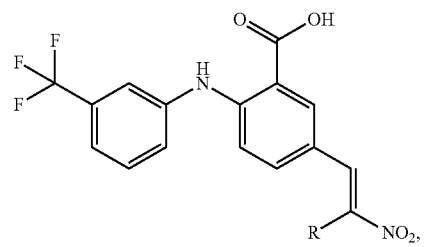

wherein R is hydrogen or a $C_{1-11}$ alkyl, or a pharmaceutically acceptable salt thereof;

a compound of Formula V:

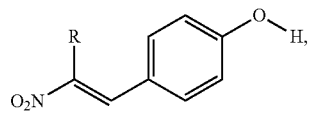

wherein R is hydrogen, or a pharmaceutically acceptable salt thereof, and any combination thereof; and a carrier.

4. The method of claim 3, wherein the nitroalkene nonsteroidal anti-inflammatory drug (NA-NSAID) is selected from the group consisting of:

21
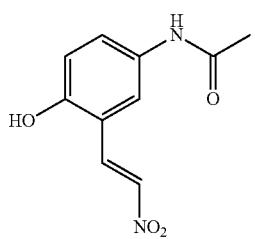 [SMILES: CC(=O)Nc1ccc(O)c(/C=C/[N+](=O)[O-])c1]
or a pharmaceutically acceptable salt thereof;
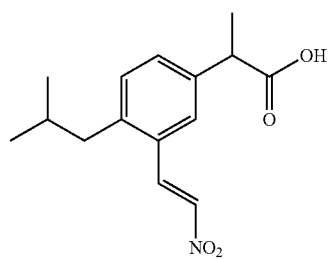 [SMILES: CC(C)Cc1ccc(C(C)C(=O)O)cc1/C=C/[N+](=O)[O-]]
22
or a pharmaceutically acceptable salt thereof;
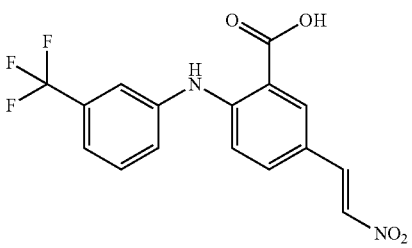 [SMILES: O=C(O)c1cc(/C=C/[N+](=O)[O-])ccc1Nc1cccc(C(F)(F)F)c1]
or a pharmaceutically acceptable salt thereof;
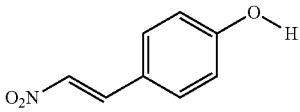 [SMILES: O=[N+]([O-])/C=C/c1ccc(O)cc1]
or a pharmaceutically acceptable salt thereof; and any combination thereof.
* * * * *